United States Patent [19]

Jennen et al.

[11] E Re. 30,476

[45] Reissued Jan. 13, 1981

[54] DEVICES FOR THE FOLD-FREE STRETCHING AND HOLDING OF LIQUID CRYSTAL FILMS

[75] Inventors: Friedrich Jennen, Bergisch-Gladbach; Hermann Linden, Cologne, both of Fed. Rep. of Germany

[73] Assignee: Bayer Aktiengesellschaft, Leverkusen, Fed. Rep. of Germany

[21] Appl. No.: 953,283

[22] Filed: Oct. 20, 1978

Related U.S. Patent Documents

Reissue of:

[64] Patent No.: 4,079,529
Issued: Mar. 21, 1978
Appl. No.: 703,152
Filed: Jul. 7, 1976

U.S. Applications:

[63] Continuation of Ser. No. 581,323, May 27, 1975, abandoned.

[51] Int. Cl.[2] ..... D05C 1/04; G09F 1/12; A47G 5/00

[52] U.S. Cl. ..... 38/102.2; 40/152; 160/380

[58] Field of Search ..... 38/102, 102.1, 102.91, 38/102.2; 160/378, 380; 350/160 LC; 40/152, 156, 155, 10 R, 125 G

[56] References Cited

U.S. PATENT DOCUMENTS

| | | | |
|---|---|---|---|
| 2,760,299 | 8/1956 | Gable et al. | 38/102.2 |
| 3,408,759 | 11/1968 | Rotheraine et al. | 40/152 |
| 3,596,385 | 8/1971 | Tachibana | 38/102.2 |
| 3,729,045 | 4/1973 | McDonald | 160/380 |
| 3,885,333 | 5/1975 | Zachary | 38/102.2 |

*Primary Examiner*—Patrick D. Lawson
*Attorney, Agent, or Firm*—Sprung, Felfe, Horn, Lynch & Kramer

[57] ABSTRACT

A frame for holding and stretching liquid crystal films for thermographic diagnosis of cutaneous and subcutaneous disorders. A foil coated with the liquid crystal is held and stretched by the frame. The frame comprises an [outer] *inner* member 1 which is secured to [inner] *outer* member 2 by clips 3 registering in openings 8. The frame members are contoured so the stretching is effected without formation of folds.

16 Claims, 7 Drawing Figures

DEVICES FOR THE FOLD-FREE STRETCHING AND HOLDING OF LIQUID CRYSTAL FILMS

Matter enclosed in heavy brackets [ ] appears in the original patent but forms no part of this reissue specification; matter printed in italics indicates the additions made by reissue.

This application is a continuation of Ser. No. 581,323, filed May 27, 1975, now abandoned.

This invention relates to a device for the foldfree stretching and holding of liquid crystal films.

Liquid crystal films intended to be used for thermographic diagnosis of cutaneous or sub-cutaneous disorders, for example breast cancer tumours, have to be stretched without any folds. At the same time, they must not be overstretched. The most common method of stretching and fixing very thin liquid crystal films is to insert the films into smooth frames and bond them in position. This method is time-consuming and, once the film has been inserted, any errors in its positioning cannot be corrected.

The object of the invention is to provide a frame in which a liquid crystal film can be automatically stretched free from any folds without at the same time being destroyed, the film being fixed in position once it has been stretched across the frame.

According to the invention there is provided a device for the fold-free stretching and holding of liquid crystal films, consisting of a substantially rectangular outer frame having an [external] *inner* centering edge for an insertable inner frame comprising an [inner] *external* centering edge, wherein the inner boundary of the [inner] *outer* frame is in the form of a stretching collar, the surface of the collar facing the *inner* centering edge being bevelled, the lower edge of the stretching collar being rounded off and its surfaces being smooth, whilst the surface of the stretching collar facing away from the *inner* centering edge is also bevelled, but at a steeper angle than that surface facing the *inner* centering edge, the corners of the inner boundary of the outer and inner frames being rounded off, and wherein the outer *inner* frame comprises a stretching groove which cooperates with the stretching collar and the surface of the [outer] *inner* frame directed towards the inner *centering* edge of the [inner] frame is bevelled parallel to the bevel of the stretching collar.

The particular advantage of the device according to the invention is that a liquid crystal film may be placed loosely over the frame in its open position, after which the frame can be closed. The liquid crystal film is carefully stretched by being drawn over the rounded edges of the stretching collar. By virtue of the fact that the surfaces are smooth (through the polished surfaces of the injection mould), the liquid crystal film slides over the surface of the stretching collar during stretching without being damaged. The corners of the inner boundary of the outer frame and inner frame are rounded off in such a way that the liquid crystal film cannot develop any fold in this zone either. After stretching, the film is kept in its stretched position by the frame.

In a preferred embodiment of the device according to the invention, clips are arranged on the outer frame which are designed to engage in corresponding openings formed in the inner frame. By virtue of this measure, the inner and outer frame are held together and the liquid crystal film is fixed in its stretched position. The outer and inner frames can only be taken apart using special tools. This measure precludes unauthorized removal of the liquid crystal film.

In another embodiment of the device according to the invention, a double adhesive tape is arranged on the inside of the outer frame. This is another safeguard against removal of the liquid crystal film from the frame.

One exemplary embodiment of the device according to the invention is described in more detail in the following with reference to the accompanying drawings, wherein.

Figure 1:
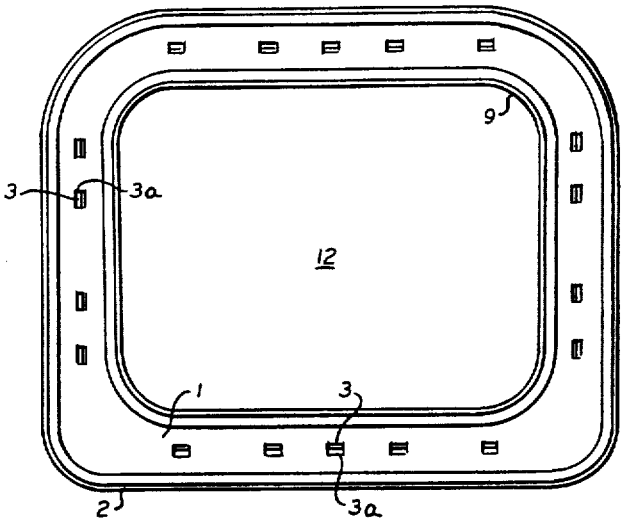
FIG. 1 shows the two frame parts assembled to each other viewed from the under side.

The frame device according to FIG. 1 comprises two registering parts, the [outer] *inner* frame 1 and the [inner] *outer* frame part 2. The [outer] *inner* part 1 fits snugly in the [inner] *outer* part 2. When pressed against each other the clips 3 projecting from the [inner] *outer* frame 2 snap into corresponding apertures 3a in the [outer] *inner* frame 1 so that the two frame parts are firmly fixed to each other. The screen area 12 is defined (circumscribed) by the inner rim [5] *14* of [outer and] inner frame [parts] *1*. The corners 9 of the inside rims of the outer and inner frame parts are rounded off at a radius of 20–25 mm.

Figure 6:
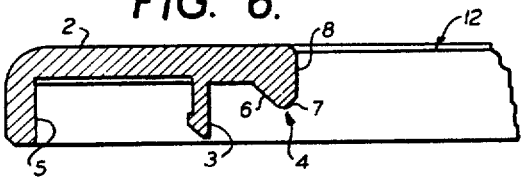
FIG. 6 is a cross section along C—D in FIG. 4.

Referring to FIG. 6, the [inner] *outer* frame part 2 is provided at its inner edge with a particularly formed bead or stretching collar 4. Stretching collar 4 is defined by three faces: Face 8 having a steep slope seen from a direction perpendicular to the screen plane, followed by a rounded lower part or curved face 7 which changes over again into an ascending plane face (with respect to the screen plane 12). The face 6 has a moderate slope compared with face 8. This particular contour of the peripheral bead or stretching collar is important for stretching the foil. The angle between the face 8 and the surface normal of the screen plane 12 is about 5°. The ascending face 6 includes with the surface normal an angle of about 45°. The radius of the curved face 7 is about 1.2 mm. The bevelled face 6 is turned to the inner centering edge 5 whereas face 8 is turned away from edge 5 and faces to the screen plane. The inner centering edge or rim 5 is provided by the part of the [inner] *outer* frame 2 which is bent 90° from the screen plane.

Figure 7:
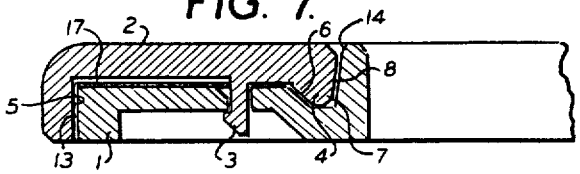
FIG. 7 shows a cross sectional view when the two frame parts are assembled.

The profile of the [outer] *inner* frame 1 is adapted to the profile of the [inner] *outer* frame 2. The registering relationship is shown in FIG. 7. Note in particular that the external centering edge 13 of [outer] *inner* frame 1 is contiguous to the inner centering edge 5 of the [inner] *outer* frame 2, and the peripheral stretching groove 11 cooperates with stretching collar 4 of the [inner] *outer* frame 2, when both parts are assembled, shown in FIG. 7. The inner rim of the [outer] *inner* frame part 1 is rounded of as shown at 14.

Figure 2:
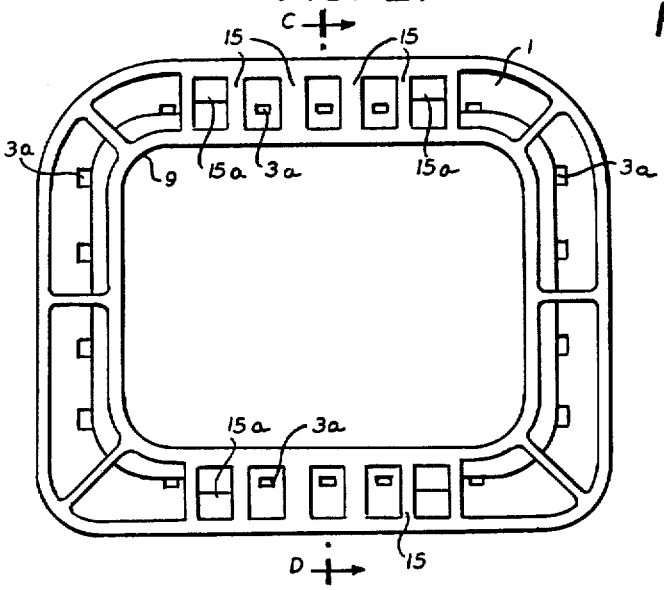
FIG. 2 shows the lower [outer] *inner* frame part in more detail and again viewed from the under side.

Referring to FIG. 2, the ribs 15 in the lower frame part are only serving for reinforcement. Openings 15a are provided for mounting of the assembled frames on holder for study of the liquid crystal films. Both frame parts are made for instance from polystyrene by injection molding technique.

Figure 3:
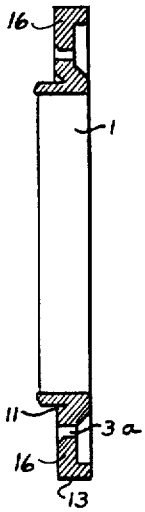
FIG. 3 shows a cross section through the [outer] *inner* frame part along line C—D in FIG. 2.
Figure 4:
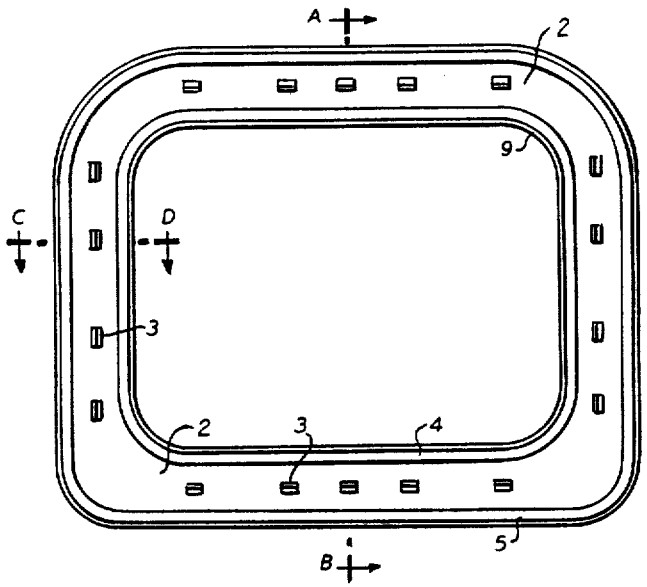
FIG. 4 shows the upper [inner] *outer* frame part from the under side.
Figure 5:
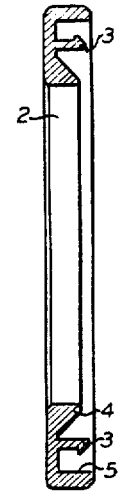
FIG. 5 represents a cross sectional view along A—B.

A foil coated with liquid crystals is assembled within the two frame members in the following manner: The foil is first loosely put onto the [outer] *inner* frame member 1, the foil being cut to a rectangular format in such a manner that the foil projects over the inner rim 14 of [outer] *inner* frame 1 and ends within face 16 (see FIG. 3) between the openings 3a for the [cramps] *clips* 3 and the external centering edge 13. Then the [inner] *outer* frame member 2 is fitted to the [outer] *inner* frame member 1 and both parts are pressed together so that the clips 3 are snapped into the openings 3a in the [outer] *inner* frame 1. When pressing both frame members together, the clips are protruding through the foil. In this assembling step the foil is slightly pulled over the inner rounded rim 14 of [outer] *inner* frame 1 and the contour faces of the stretching collar 4. By pressing the foil into the stretching groove 11 of the [outer] *inner* frame part in the assembling step, the foil is moderately stretched in the screen plane. Surprisingly, it has been found that creases and warping can be strictly avoided in this way. This is a necessary requirement for obtaining a high image quality when using a liquid crystal foil for medical diagnostic purposes. On the other hand the stretching effect must not be too much in order to prevent the foil from tearing. Further to prevent tearing the contour faces 6, 7, 8 (FIG. 7) of the stretching collar 4 should be very smooth. This is easily achieved by polished surfaces in the injection molding form. Regarding the delicate problem of achieving an absolutely smooth foil surface in the screen plane, the frame members according to the invention constitute a unique solution for this particular object.

A further improvement for securing the foil may be achieved by providing adjacent faces in the region beneath clip 3, for instance face 16 (FIG. 3) with double sided adhesive tape 17 (FIG. 7) so that the marginal zone of the foil sticks to either one of the frame parts 1 and 2.

Normally the clips 3 provide for a reliable connection between the two frame members. With higher requirements the two frame members may also be welded to each other.

What is claimed is:

1. A device for the fold-free stretching and holding of liquid crystal films, comprising a substantially rectangular outer frame having an [external] *inner* centering edge and an insertable inner frame comprising an [inner] *external* centering edge, wherein the inner boundary of the [inner] *outer* frame is in the form of a stretching collar, the surface of the collar facing the inner [frame] centering edge being bevelled, the lower edge of the stretching collar being rounded off and its surfaces being smooth, the surface of the stretching collar facing away from the inner [frame] centering edge being bevelled at a steeper angle than that surface facing the inner [frame] centering edge, and wherein the [outer] *inner* frame comprises a stretching groove which cooperates with the stretching collar and the surface of the [outer] *inner* frame directed towards the [inner edge] *stretching collar* of the [inner] *outer* frame is bevelled parallel to the bevel of the stretching collar, the corners of the inner [boundry] *boundary* of the outer and inner [frame] *frames* being rounded off, the outer frame being insertable in the [inner] *outer* frame by cooperation of the inner and external centering edges and cooperation of stretching collar and stretching groove.

2. A device as claimed in claim 1, wherein clips arranged on the [inner] *outer* frame engage in openings formed in the [outer] *inner* frame.

3. A device as claimed in claim 1, wherein a double adhesive tape is arranged on the inside of the outer frame.

4. A device as claimed in claim 2, wherein a double adhesive tape is arranged on the inside of the outer frame.

5. A device as claimed in claim 1, wherein said corners are rounded with a radius of 20 to 25 mm.

6. A device as claimed in claim 4 wherein said corners are rounded off with a radius of 20 to 25 mm.

7. A device as claimed in claim 2, wherein the clips are spaced from and disposed outwardly of the [inner] *outer* frame stretching collar.

8. A device as claimed in claim 7, wherein the clips are disposed intermediate the [inner] *outer* frame stretching collar and the inner [frame] centering edge.

9. A device as claimed in claim 6, wherein the clips are spaced from and disposed outwardly of the [inner] *outer* frame stretching collar.

10. A device as claimed in claim 9, wherein the clips are disposed intermediate the [inner] *outer* frame stretching collar and the inner [frame] centering edge.

11. A device according to claim 2, wherein said corners are rounded off with a radius of 20 to 25 mm and the clips are spaced from and disposed outwardly of the [inner] *outer* frame stretching collar.

12. A device as claimed in claim 11, wherein the clips are disposed intermediate the [inner] *outer* frame stretching collar and the inner [frame] centering edge.

13. A device according to claim 1, the inner frame being inserted in the outer frame, and a liquid crystal film being held in the frame by being drawn over the rounded edges of the stretching collar.

14. A device according to claim 2, the inner frame being inserted in the outer frame, and a liquid crystal film being held in the frame by being drawn over the rounded edges of the stretching collar.

15. A device according to claim 7, the inner frame being inserted in the outer frame, and a liquid crystal film being held in the frame by being drawn over the rounded edges of the stretching collar.

16. A device according to claim 8, the inner frame being inserted in the outer frame, and a liquid crystal film being held in the frame by being drawn over the rounded edges of the stretching collar.

* * * * *

UNITED STATES PATENT AND TRADEMARK OFFICE

CERTIFICATE OF CORRECTION

PATENT NO. : Reissue 30,476

DATED : January 13, 1981

INVENTOR(S) : Friedrich Jennen et al

It is certified that error appears in the above–identified patent and that said Letters Patent are hereby corrected as shown below:

Title Page insert --Foreign Application Data

June 11, 1974, Germany.....24 28 235--,

Col. 2, line 66, delete "of" and insert --off--.

Signed and Sealed this

*Thirteenth* Day of *October 1981*

[SEAL]

*Attest:*

GERALD J. MOSSINGHOFF

*Attesting Officer*

*Commissioner of Patents and Trademarks*